United States Patent [19]

Drewes et al.

[11] 4,315,514
[45] Feb. 16, 1982

[54] METHOD AND APPARATUS FOR SELECTIVE CELL DESTRUCTION

[75] Inventors: William Drewes, 100 Ellison Ave., Bronxville, N.Y. 10708; Martin Levine, Hastings-on-Hudson, N.Y.

[73] Assignee: William Drewes, Bronxville, N.Y.

[21] Appl. No.: 148,058

[22] Filed: May 8, 1980

[51] Int. Cl.³ ............................................. A61B 5/00
[52] U.S. Cl. .................................... 128/653; 128/660; 128/24 A
[58] Field of Search ................................. 128/660–663, 128/24 A, 653; 73/579, 601–602

[56] References Cited

U.S. PATENT DOCUMENTS

| | | | |
|---|---|---|---|
| 3,499,436 | 3/1970 | Balamuth | 128/24 A |
| 3,640,271 | 2/1972 | Horton | 128/662 |
| 3,735,755 | 5/1973 | Eggleton et al. | 128/24 A |
| 3,901,074 | 8/1975 | Douglas | 73/579 |
| 3,958,559 | 5/1976 | Glenn et al. | 128/660 |
| 4,043,181 | 8/1977 | Nigani | 73/631 |
| 4,216,766 | 8/1980 | Duykers et al. | 128/24 A |
| 4,223,676 | 9/1980 | Wuchinich et al. | 128/24 A |

Primary Examiner—Robert W. Michell
Assistant Examiner—Francis J. Jaworski
Attorney, Agent, or Firm—Hubbell, Cohen, Stiefel & Gross

[57] ABSTRACT

Method for destroying selected cells in a host without damage to non-selected cells comprises selecting a transmission path from an energy source (12) to the selected cells (30); determining one or more of the resonant frequencies of the selected cells (30); selecting as a destructive frequency one of the resonant frequencies at which the transmissibility of the selected cells (30) is higher than the transmissibility of the non-selected cells in the transmission path; and transmitting energy from the source (12) at the destructive frequency along the path with sufficient intensity to destroy the selected cells (30) without destroying the non-selected cells. Apparatus for practicing the method is also disclosed.

6 Claims, 3 Drawing Figures

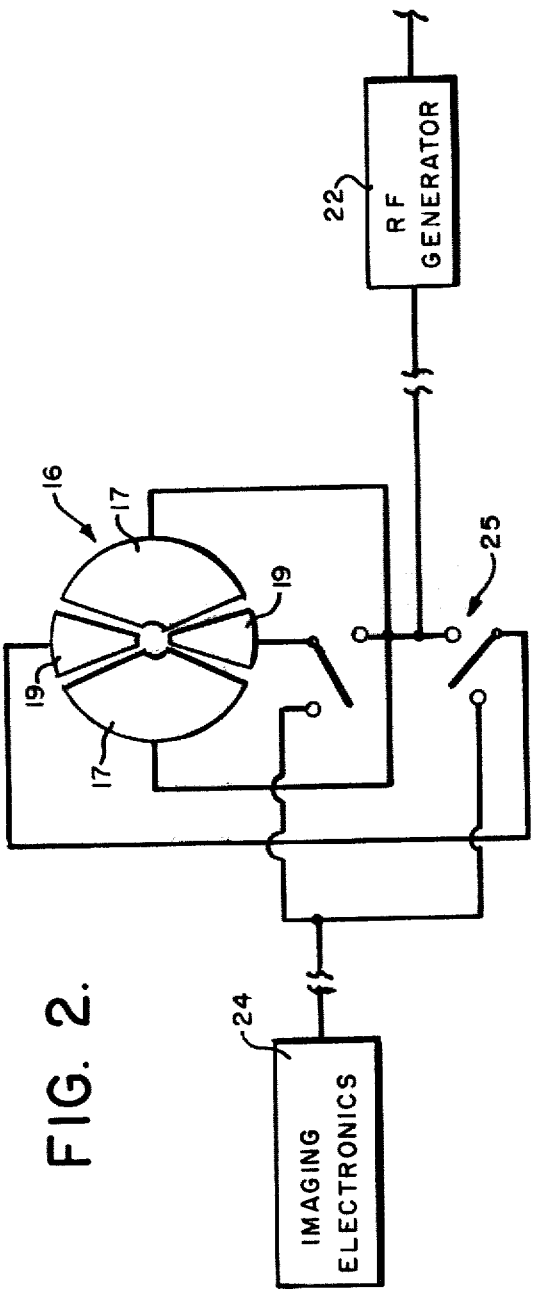
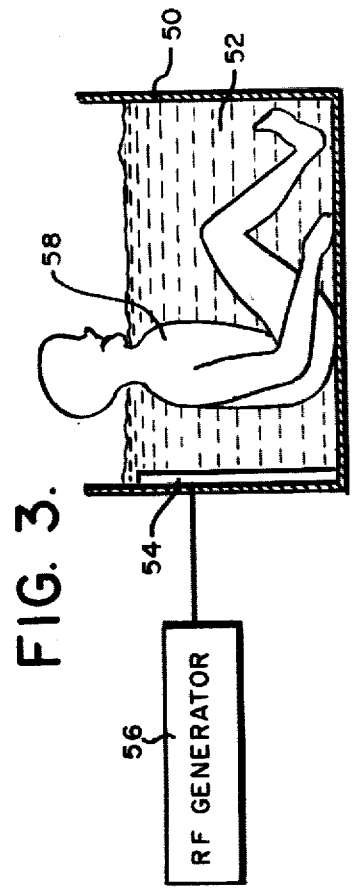
FIG. 2.
FIG. 3.

METHOD AND APPARATUS FOR SELECTIVE CELL DESTRUCTION

TECHNICAL FIELD

This invention pertains to the destruction of tissue cells, such as tumorous tissue cells, and more specifically to the non-invasive selective destruction of such cells by ultrasonic transmissions.

BACKGROUND ART

The use of ultrasound for destroying predetermined groups of tissue cells, such as tumors, is known. See, for example U.S. Pat. Nos. 3,958,559, 3,237,623 and 3,117,571. Typically, a piezoelectric ultrasonic generator driven by an rf amplifier is coupled to an ultrasonic lens of known focal length. The locus of the cells to be destroyed is first determined by employing, for example, known pulse-echo imaging techniques. During this phase, the ultrasonic transducer is driven at a sufficiently low intensity to preclude tissue cell damage. Once the locus of the target cells is fixed, the lens is focused on the target area, as by means of a stereotaxic device, and the intensity of the ultrasound is increased to a level sufficient to effect tissue destruction by thermal heating.

Because this technique relies on thermal heating to destroy the target cells, it is necessary to precisely focus the ultrasonic beam to avoid damage to surrounding tissue cells. For example, when the target area is in the brain, imprecise focusing can cause extensive damage. However, precise focusing is not always possible, as where the target area is smaller than the focal zone of the lens, or where the target cells are transient, as in the case of leukemia.

Another known ultasonic technique involves the direct application of ultrasound to the target area by means of a vibrating surgical instrument, often in the form of a probe. Where internal cells are to be destroyed, the probe must be surgically inserted into the patient to accomplish direct application, whereupon the instrument is vibrated with sufficient intensity to destroy the target cells. See, for example, U.S. Pat. Nos. 4,136,700, 4,063,557, 3,896,811, 3,823,717, 3,805,787, 3,589,363, 3,565,062 and 3,352,303. Like the focused ultrasonic beam technique described above, the use of vibrating probes is accompanied by the risk of damage to surrounding tissue cells, especially when the target area is small. Furthermore, the vibrating probe is useless in the case of transient target cells and is disadvantageous insofar as it requires surgical insertion to destroy internal cell groups.

U.S. Pat. Nos. 3,499,436 and 3,499,437 are of interest insofar as they disclose means for transmitting sonic energy to an organism for analgesic and other purposes.

DISCLOSURE OF THE INVENTION

Cells exhibit several resonant frequencies corresponding, for example, to distortion of the cell wall, distortion of the nucleus, etc. As with all objects, if a cell is impacted with energy at a predetermined frequency, the portion of the input energy converted into mechancial energy, i.e. motion, will be significantly enhanced if the input frequency is at one of the resonant frequencies of the cell. The mechanical response of an object to a given input driving frequency is defined by its transmissibility T where $$T = \frac{1}{\sqrt{\left[1 - \frac{w^2}{w_n^2}\right]^2 + [2L\, w/w_n]^2}} \quad \text{(EQ. A)}$$

In Equation A, w is the frequency of the input driving energy, $w_n$ is the resonant frequency of the object, and is the damping coefficient of the object. Assuming, for example, that an object has a damping ratio of 0.25, the transmissibility decreases from a value of 4.0 at resonance ($w = w_n$) to 1.55 at 25% above resonance ($w = 1.25\, w_n$). In other words, the percentage of the input driving energy converted to mechanical energy in the object at resonance is almost three times as great as when the input driving energy is at a frequency 25% above resonance. The equation also shows that as the damping coefficient increases, the transmissibility decreases and that at damping coefficients above 0.5, the resonant effect is virtually nil. Generally, objects exhibit different damping coefficients at each of their different resonant frequencies.

It will therefore be apparent that if an object having a relatively low damping coefficient at a particular resonant frequency is vibrated at that frequency, the amplitude of the input energy required to destroy the object will be significantly lower than that required at a non-resonant input frequency. The classic example is a singer shattering a glass.

The method and apparatus of the invention rely on the phenomenon of resonance to destroy abnormal cells, such as cells comprising a tumor. Because of the difference in structure as between normal tissue cells and abnormal cells, their resonant frequencies also differ. Therefore, if a resonant frequency of the abnormal tissue cells can be found at which the transmissibility of the abnormal cells is sufficiently higher than the transmissibility of the surrounding healthy tissue cells, the abnormal cells can be vibrated at that frequency with sufficient intensity to destroy them. The healthy cells, because they exhibit a low transmissibility at the destructive frequency selected, will not be damaged in the process.

In order to select a suitable resonant frequency for use in destroying the abnormal cells, it will be apparent from Equation A that the various resonant frequencies and corresponding damping coefficients of the abnormal cells must be determined. To do so, a biopsy of the abnormal cells is preferably taken. The resonant frequencies of the biopsy cells may then be determined by impacting the biopsy cells with energy over the expected range of useful resonant frequencies, for example, 0.1 MHz to 4 MHz. If cell movement is monitored during this procedure, the resonant frequencies will be apparent from amplified movement of the cells at those frequencies. By way of example, the biopsy cells may be impacted by ultrasound from a piezoelectric crystal driven by an rf generator and cell movement detected by a laser interferometer of sufficient resolution. Once the resonant frequencies are known, high frequency pulse techniques may be used to determine the corresponding damping coefficients.

A transmission path through the patient's body to the abnormal cells is then selected, the object being to minimize attenuation and reflection losses during transmission. Once the preferred path is selected, the transmissibility of each of the different types of normal tissue cells in the transmission path is determined for each of the different resonant frequencies of the abnormal cells. Again, it will be apparent from Equation A that this requires knowledge of the resonant frequencies and corresponding damping coefficients of the healthy tissue cells. These may be determined by using the same techniques employed for determining the resonant frequencies and corresponding damping coefficients of the abnormal cells. However, it will not be necessary to repeat these calculations for each patient since the structure of normal tissue cells do not vary from person to person.

At this point, one of the resonant frequencies of the abnormal cells is selected as the destructive frequency. Two factors are involved in making this selection. First, at the resonant frequency selected, the abnormal cells must exhibit a sufficiently low damping coefficient to insure a significant resonant effect. Secondly, the normal tissue cells in the transmission path must exhibit a relatively low transmissibility at the destructive frequency selected. This is necessary to avoid damage to the normal tissue cells during the destruction process.

Once the preferred destructive frequency is selected, the intensity required to destroy the abnormal cells is calculated. To do so, it is necessary to take into account the attenuation and reflection losses as the destructive beam passes through the intervening body tissue before impacting the abnormal cells. In addition, it is presently preferred that a medium, such as water, be disposed between the patient and the source of the destructive beam, and losses resulting from transmission through this medium should also be taken into account.

The patient is then positioned such that ultrasonic radiation from the source is transmitted along the preferred transmission path to the abnormal cells whereupon the source is activated to deliver ultrasonic radiation at the intensity and frequency selected, the radiation being continued until the abnormal cells are destroyed. Because of the high frequencies involved, the time period required to destructively vibrate the cells is minimal. Consequently, effects due to heating of neighboring healthy tissue will be negligible.

If the number of abnormal cells is sufficiently small, they will likely be carried out of the body by its normal waste systems. Alternatively, when the growth is large, surgical removal may be necessary. However, because the abnormal cells are already dead, removal of all the abnormal cells is not necessary. Therefore, damage to surrounding healthy tissue is avoided even when surgical removal is required.

As will be apparent hereinafter, the method and apparatus of the invention may be used for treating non-localized abnormal cell growths, such as those found in skin cancer patients. It is also valuable in treating conditions wherein the abnormal cells are transient, as in the case of leukemia.

These as well as further features and advantages of the method and apparatus of the present invention will be apparent from the following detailed description and annexed drawings of the presently preferred embodiments thereof.

BRIEF DESCRIPTION OF THE DRAWINGS

In the drawings:

FIG. 2 is a diagrammatic illustration of the preferred switching network for connecting the piezoelectric crystal to the imaging electronics and rf generator; and FIG. 3 is a modified apparatus for practicing the method of the present invention.

DETAILED DESCRIPTION OF THE PREFERRED EMBODIMENTS

Figure 1:
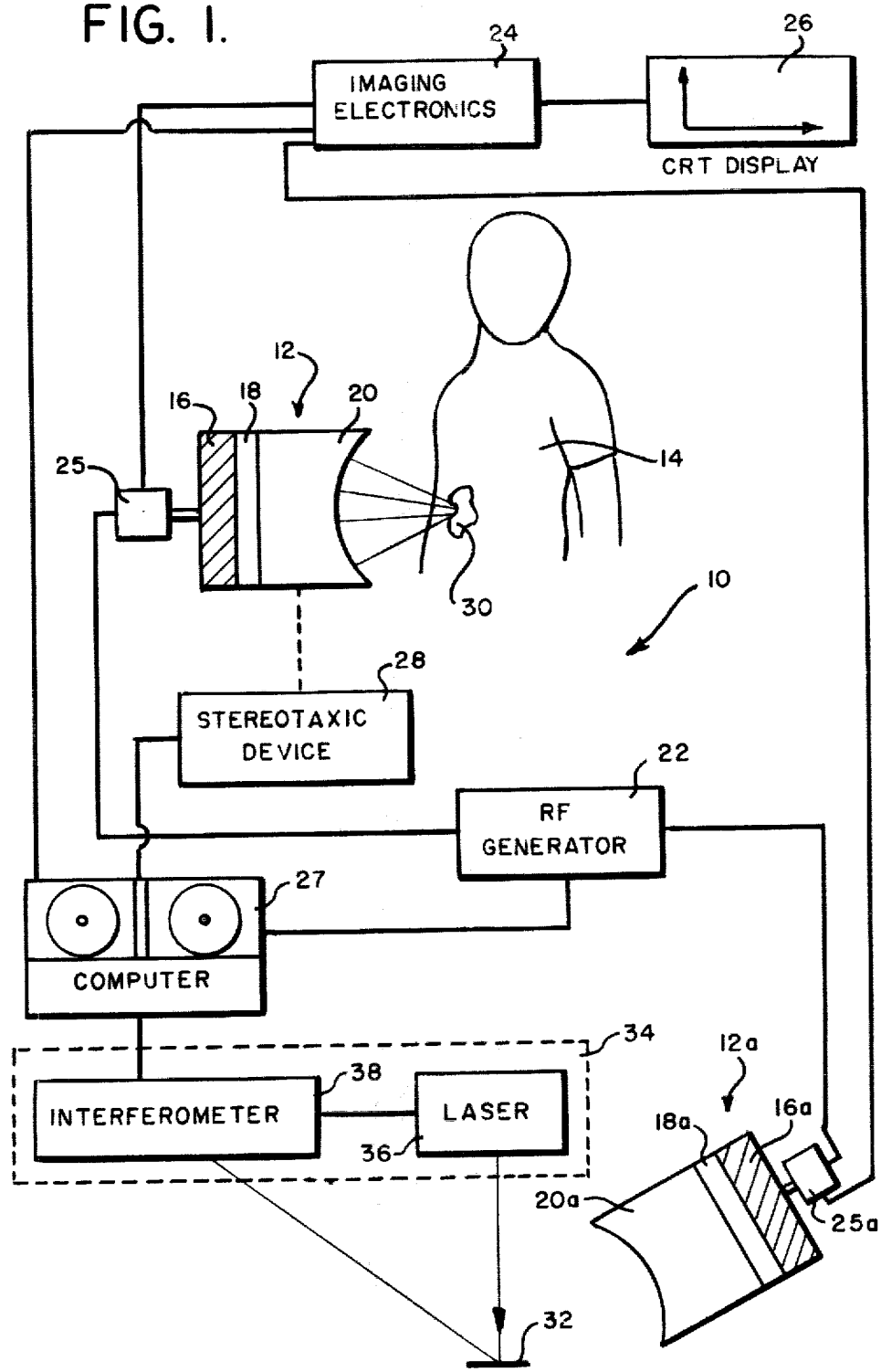
FIG. 1 is a diagrammatic illustration of the preferred apparatus for carrying out the method of the present invention.

Referring now to FIG. 1, the preferred system 10 for practicing the present invention is diagrammatically illustrated. As shown, the system 10 includes ultrasonic transmitter-receiver means 12 for focusing ultrasonic energy on the patient 14. Ultrasonic transmitter-receiver means 12 may comprise, for example, a piezoelectric crystal transducer 16 of conventional flat disc-like geometry, interfaced, via a suitable coupling medium 18, with the flat surface of a plano-concave lens 20. The lens 20 may be comprised of any suitable material, such as polystyrene. The coupling medium 18 may comprise water, oil or the like, and is utilized to minimize reflection losses between the crystal 16 and the lens 20. Alternatively, the crystal 16 may be bonded directly to the lens 20.

Excitation of the piezoelectric crystal 16 by a suitable radio frequency generator 22 results in conversion of the exciting energy into an essentially collimated beam of ultrasound which is transmitted via the coupling medium 18 to the lens 20 where it is focused on the patient 14. In the exploratory stage, the rf generator 22 preferably drives the crystal 16 to produce a series of short ultrasonic pulses which are focused by the lens 20 on the suspected locus of the tumor or other growth 30. The pulses are preferably in the frequency range from about 1 MHz to about 3 MHz. The pulses should be of relatively low intensity and sufficiently short to avoid damage to the body tissue. To minimize attenuation losses resulting from reflection, the lens 20 is preferably coupled to the patient's skin by a liquid transmission medium, such as water. While means for effecting liquid coupling are not illustrated in FIG. 1, such means are well known in the art. See, for example, U.S. Pat. No. 3,237,623, the content of which is hereby incorporated herein by reference in its entirety. As an alternative to the use of a liquid transmission medium, the lens, provided it has a suitably short focal length, may be placed directly against the body and coupled to the skin, as by a cream.

As the short duration ultrasonic pulses penetrate the body and impact the internal structures thereof, echo pulses are returned to the lens face 20. The echo pulses represent reflections from the different biological structures which present different acoustical impedances to the traveling ultrasonic pulses as a result of differences in density and elasticity. As the ultrasonic echo pulses strike the lens 20, they are transmitted to the piezoelectric crystal 16 which converts them into radio frequency energy. This energy is detected by suitable imaging electronics 24 tuned to the carrier frequency of the rf generator 22.

Referring to FIG. 2, the crystal 16 is sectioned to accommodate simultaneous transmission and reception of ultrasonic energy. As shown, crystal 16 is preferably subdivided into two major sectors 17 and two minor sectors 19. The major sectors 17 are coupled to the rf generator 22 and thus serve as a source of ultrasonic pulses. For reasons that will be apparent hereinafter, a switching network 25 is provided for connecting the minor sectors 19 to either the rf generator 22 or the imaging electronics 24. During the exploratory stage, the minor sectors 19 are connected to the imaging electronics 24 and thus serve to detect the returning echo pulses.

The imaging electronics 24 produce output voltage pulses, the magnitudes of which are proportional to the amplitude of the echo pulses. As shown, the output pulses are preferably displayed on the CRT display 26. There are several techniques for displaying meaningful information concerning the configuration of the internal structure of the patient 14 on the CRT display 26, any one of which may be used herein. For example, echo pulses may be displayed as spikes of varying height along the time base sweep line on the screen, with the height of each spike being indicative of the relative reflectivity of the biological target, and the displacement of the spike with respect to the point of origin of the sweep line being indicative of the distance between the target and the crystal 16. In another technique, the electronic beam of the CRT is intensity-modulated by the returning echo pulses and deflected in synchronism with the ultrasonic beam as it scans a particular area of the body. It will be apparent that with either technique it is possible to definitively determine the depth coordinates of the abnormal cells 30 which exhibit a different reflectivity than that of the surrounding tissue. Once determined, the coordinates of the abnormal cells 30 are preferably stored in a computer 27. However, and as will be apparent hereinafter, destruction of abnormal cells according to the present invention does not require a precise determination of the locus of the cells to be destroyed.

To facilitate scanning of the patient 14 with the ultrasonic beam during the exploratory stage, the means 12 is preferably supported by a stereotaxic device 28. Since the construction of such devices is well known in the art, further description thereof is deemed unnecessary. See, for example, the stereotaxic device disclosed in U.S. Pat. No. 3,237,623, the content of which is incorporated by reference herein in its entirety. As diagrammatically shown, movement of the stereotaxic device 28 is preferably controlled by the computer 27 which may be preprogrammed to scan all or part of the patient's body.

Once the abnormal cells 30 are located, a biopsy 32 is taken. For reasons that will become apparent hereinafter, the biopsy is used to determine the resonant frequencies and corresponding damping coefficients of the abnormal cells. The resonant frequencies may be determined, for example, by employing laser interferometry. As diagrammatically illustrated in FIG. 1, the biopsy cells 32 are impacted by ultrasound using, for example, an ultrasonic transmitter-receiver means 12a. The means 12a may be identical to the means 12 described hereinabove, and thus preferably includes crystal 16a, coupling medium 18a, and lens 20a. Like the crystal 16, the crystal 16a preferably includes major sectors 17a connected to rf generator 22, minor sectors 19a, and a switching network 25a for selectively coupling the minor sectors to either the rf generator 22 or the imaging electronics 24. Of course, rather than using the rf generator 22 and imaging electronics 24, a separate rf generator and imaging electronics could be used. In fact, if desired, the means 12a could be eliminated altogether and the transmitter receiver means 12 used for impacting the biopsy cells 32 as well. However, because it is presently contemplated that analysis of the biopsy cells 32 will be carried out in a different room than patient treatment, a separate transmitter means 12a is presently preferred.

As will be apparent hereinafter, there is no necessity for liquid or other coupling between the lens 20a and the biopsy cells 32 inasmuch as there is little concern with transmission losses. In fact, although presently preferred, it is not absolutely necessary to focus the ultrasonic beam from the piezoelectric crystal 16a. Thus, if desired, the lens 20a and hence coupling medium 18a could be eliminated and the collimated ultrasonic beam from the crystal 16a simply directed at the biopsy cells 32. All that is required is that some ultrasonic energy strike the biopsy cells 32 with sufficient intensity to effect movement of the cell structures at their resonant frequencies.

In the preferred technique for detecting the resonant frequencies of the biopsy cells 32, the frequency of the rf generator 22 is gradually increased such that the frequency of the ultrasonic beam generated by the piezoelectric crystal 16a is varied over the expected useful range of resonant frequencies of the biopsy cells 32. For example, the crystal 16a may be driven over the range 0.1 MHz to 4 MHz. Thus, cells exhibit several resonant frequencies corresponding, for example, to linear motion of the nucleus, distortion of the nucleus, distortion of the cell wall, etc. The generator 22 is preferably driven over the desired frequency range by the computer 27 which may be preprogrammed for this function. During this phase, the switching network 25a is set such that both the major sectors 17a and minor sectors 19a of the crystal 16a are connected to the rf generator 22. As the generator 22 drives the crystal 16a, the laser interferometry unit 34 detects the resulting movement of the biopsy cells 32. Thus, according to known techniques, the output from the laser 36 is split into two beams. The first beam is directed at the biopsy cells 32 and reflected therefrom to the interferometer 38, while the second beam is introduced directly into the interferometer. By employing a photocell or similar device, the interferometer 38 measures the movement of the impacted object, in this case the biopsy cells 32, based on changes in the light pattern produced with the two laser beams are combined. As the ultrasonic beam from the transmitter 12a is varied over the expected resonant frequency range, the resonant frequencies of the cells 32 are indicated by amplified movement of the cell structure as detected by the interferometer 38. Laser interferometers having sufficient resolution for incorporation in the system 10 are commercially available. For example, the Model 5526A laser interferometer marketed by Hewlett-Packard is capable of measuring distance with a resolution of one millionth of an inch. As diagrammatically illustrated in FIG. 1, the resonant frequencies of the cells 32 as detected by the laser interferometer 34 are preferably stored in the computer 27 for subsequent use. Of course, at some resonant frequencies the corresponding damping coefficient of the abnormal cells will be so high that little, if any, amplified movement of the cells will occur. However, this is of little concern since, as will be apparent hereinafter, resonant frequencies at which the damping coefficient is high are of no interest.

Once the potentially useful resonant frequencies of the biopsy cells are known, the damping coefficients of the cells 32 at those frequencies are determined. Because of the frequencies involved, it is presently preferred to employ high frequency pulse techniques to determine the damping coefficients. This is preferably accomplished by first removing the coupling medium 18a and lens 20a from the crystal 16a. A relatively thin biopsy is then secured, as by cementing, directly to the front face of the piezoelectric crystal 16a. With the switching network 25a adjusted such that the minor sectors 19a are connected to the imaging electronics 24, the rf generator 22 is then activated to drive the crystal 16a to produce pulses of predetermined intensitity at one of the resonant frequencies. During this phase, the rf generator is preferably controlled by the computer 27 in which information defining the resonant frequencies of the cells 32 has been stored.

As the pulse penetrate the biopsy specimen, the imaging electronics 24 detect the intensities of the returning echo pulses reflected from the rear face of the specimen. As is well known to those skilled in the art, the damping coefficient of the cells at the resonant frequency under consideration is then determinable from the decay rate of the echo pulses. To insure the accuracy of this technique, it will be apparent that the specimens cemented to the crystal 16a must be sufficiently thin to avoid effects due to scattering of the ultrasonic beam as it passes through the specimen upon entry and again upon reflection.

To determine the damping coefficients at the other resonant frequencies of the cells 32, the procedure is simply repeated with suitable adjustment of the pulse frequency. For reasons that will be apparent hereinafter, the damping coefficients of the cells at each resonant frequency are preferably stored in the computer 27.

Once the resonant frequencies and corresponding damping coefficients of the cells 32 are known, the energy intensity required to destroy the cells 32 at each resonant frequency is determined. This determination is readily made by stepping the generator 22 to successively drive the crystal 16a at each resonant frequency of the cells 32, such stepping preferably being carried out by the computer 27 which may be preprogrammed for this function. During this phase, the switching network 25a is adjusted to couple the minor sectors 19a to the rf generator 22 such that the entire face of the crystal 16a serves as a source of ultrasonic radiation. At each resonant frequency, the intensity of the generator 22 is gradually increased until destruction of the biopsy cells 32 is detected. Cell destruction may be detected, for example, by visual observation through a microscopic element (not shown). Whatever technique is employed, the intensity level of the rf generator 22 at destruction is recorded and preferably stored in the computer 27. A new group of biopsy cells 32 is then substituted whereupon the procedure is repeated at the next resonant frequency, and so on, until the energy intensity required to destroy the biopsy cells 32 at each resonant frequency is recorded.

Of course, the actual intensity of the ultrasonic beam required to destroy the abnormal cells 30 within the patient 14 will be higher than the intensity required to destroy the biopsy cells 32. One reason for this difference is that energy will be lost by attentuation and reflection as the ultrasonic beam passes through intervening body tissues before striking the abnormal cells 30 in the patient 14. In view of these losses, it is generally preferable to position the patient 14 such that the travel distance of the ultrasonic beam through the body is minimized. However, specific situations might require using a slightly longer path. For example, in view of the relatively high losses encountered at bone tissue interfaces, and during transmission through bone itself, longer travel distances which avoid bone tissue may be desirable.

To compensate for the attenuation and reflection losses encountered during transmission through intervening body tissue, the actual magnitude of these losses must be determined. To do so, it is first necessary to select a transmission path through patient 14 to the cells 30. Once the path is selected, the actual attenuation and reflection losses resulting from transmission through that path may be calculated. Thus, the attenuation per unit distance for high frequency transmissions through various body tissues as a function of frequency is available. Such information may be found, for example, in Harris & Crede's *Shock and Vibration Handbook*, Second Edition, McGraw Hill, 1976, the content of which is incorporated herein by reference in its entirety. Accordingly, once the travel distance through each type of body tissue in the selected path is known, the total attenuation losses may be calculated. The distance traveled through each intervening body tissue may be determined, for example, by x-ray or pulse imaging techniques. The attenuation losses are preferably calculated at each resonant frequency of the cells 30.

Information sufficient to calculate losses resulting from reflection at tissue interfaces in the selected path is also available. Thus, the fraction of energy $\alpha_r$ reflected at an interface between two media is given by the equation:

$$\alpha_r = \left( \frac{Z_2 - Z_1}{Z_2 + Z_1} \right)^2 \qquad \text{(Eq. B)}$$

where $Z_1$ is the acoustic impedance of the first medium and $Z_2$ is the acoustic impedance of the second medium. The acoustic impedance $Z$ of a given medium is equal to $\rho c$ where $\rho$ is the density of the medium and c is the velocity of sound through that medium.

The acoustic impedances for various body tissues are available. See, for example, Kinsler & Frey's *Fundamentals of Acoustics*, Second Edition, John Wiley & Sons, 1962, the content of which is incorporated herein by reference in its entirety. Thus, once the tissue interfaces in the selected transmission path are identified, the fraction of the initial energy lost during transmission as a result of reflection losses is determined by summing the losses at each successive interface as calculated from Equation B. The different tissue interfaces may also be identified, for example, by employing X-ray or pulse echo imaging techniques. Inasmuch as the acoustic impedance of most materials, including body tissues, is relatively constant at frequencies above 1 megahertz, it is not necessary to recalculate reflection losses for each resonant frequency of the cells 30.

Preferably, the computer 27 is provided with a data base comprising the impedance and attenuation characteristics of the various body tissues. The computer may then be programmed to calculate the attenuation and reflection losses for any given frequency and transmission path, such programming being within the capabilities of the skilled art worker. Indeed, if, as is presently preferred, the data base of the computer 27 is augmented with information defining the anatomy of the patient 14, the computer may be programmed to determine the optimum transmission path, i.e. the path resulting in the minimum energy loss, such programming also being within the capabilities of the skilled art worker once this description is known.

Two additional factors must be taken into account to determine the actual intensity required to destroy the abnormal cells 30 in the patient 14. One is energy losses encountered during transmission through the preferred water medium between the means 12 and the patient 14. These losses comprise both attenuation losses during transmission and reflection losses at the water-skin interface. Inasmuch as the attenuation characteristics and acoustical impedance of water are well known, these losses are readily calculated. The second factor which must be taken into account is the losses resulting from transmission through the air medium between the means 12a and the biopsy cells 32. Thus, the intensity recorded at destruction of the cells 32 for each resonant frequency is based on these losses, which are not present during destruction of the cells 30 within the patient 14. The losses occasioned during transmission through the air medium between the means 12a and the biopsy cells 32 are due to attenuation losses as well as reflection losses at the air-cell interface. Inasmuch as the attenuation characteristics and acoustical impedance of air are well known, these losses are also easily calculated. Preferably, calculation of the attenuation and reflection losses resulting from transmission both through the water medium between the means 12 and the patient 14 and the air medium between the means 12a and the biopsy cells 32 are carried out by the computer 27 which may be programmed for this function, such programming again being well within the capabilities of the skilled art worker.

At this point, information sufficient to calculate the actual energy intensity required to destroy the cells 30 in the patient 14 at each resonant frequency of the cells is known. Thus, the intensity required to destroy the cells 30 in patient 14 at a given resonant frequency is equal to the intensity required to destroy the biopsy cells 32 at that frequency, increased by an amount sufficient to compensate for losses resulting from transmission through the water medium and intervening body tissue, and decreased by an amount sufficient to compensate for the absence of losses resulting from transmission through the air medium between the means 12a and the biopsy cells 32. These calculations are preferably carried out by the computer 27 which may be preprogrammed for this function. The results are preferably stored in the computer 27 for subsequent use.

The intensities and frequencies of a plurality of ultrasonic beams potentially useful for destroying the cells 30 are now known. Of these, the optimum destructive beam is selected. This requires consideration of two factors. The first is the damping coefficient of the target cells at the destructive frequency selected. Thus, as is apparent from Equation A, the resonant effect imparted to the target cells at a particular frequency is a function of the damping coefficient of the cells at that frequency. It can be shown from Equation A that if the damping coefficient is 0.5 or higher, the resonant effect is virtually nil. To insure that a substantial resonant effect is imparted to the target cells 30 by the selected destructive beam, the damping coefficient of the cells 30 at the selected frequency should be less than 0.5 and preferably 0.2 or less. Assuming a damping coefficient of 0.2 or less is desired, any potentially destructive resonant frequency at which the cells 30 exhibit a damping coefficient higher than 0.2 may be eliminated.

The second factor is the potential for damage to intervening body tissue. Thus, if the destructive beam selected for resonating the target cells 30 imparts a significant resonant effect to the intervening body tissue as well, it may result in damage to that tissue. Such a result is clearly undesirable. From Equation A, it will be apparent that once the resonant frequencies and corresponding damping coefficients of the various intervening body tissues are known, the resonant effect that would be imparted to those tissues at each potentially destructive resonant frequency may be determined. The resonant frequencies and corresponding damping coefficients of the intervening body tissues may be determined, for example, by employing the techniques described hereinabove for determining the resonant frequencies and damping coefficients of the cells 32.

In any event, once the resonant effect that would be imparted to the various intervening body tissues at each potentially destructive resonant frequency is known, the potentially destructive frequency imparting the least resonant effect to the intervening body tissue is preferably selected. In practice, this selection will preferably be performed by the computer 27, which may be preprogrammed for this purpose. Such programming is well within the capabilities of the skilled art worker once this description is known.

In a modified procedure, the technique for selecting a destructive beam that will avoid significant damage to intervening body tissue may be somewhat simplified. Thus, it may be shown from Equation A that when there is a difference of approximately 25% or more between the input frequency w and the resonant frequency $w_n$ of the object, the resonant effect imparted to the object is virtually non-existent. Accordingly, damage to intervening body tissue may be avoided by selecting a destructive resonant frequency exhibiting a difference of 25% or more from the resonant frequencies of the intervening body tissues.

Whatever technique is employed, once the preferred destructive beam is selected, the means 12 is positioned to focus the beam from the crystal 16 along the optimum transmission path through patient 14. The rf generator 22 is then adjusted to drive the crystal 16 at the frequency and intensity of the selected destructive beam. During this phase, the switching network 25 is adjusted to connect the minor sectors 19 to the generator 22 whereby the entire face of the crystal 16 serves as a source of ultrasonic energy.

The ultrasonic transmission from the means 12 is continued until the target cells 30 are destroyed. A good approximation of the time required for destruction of the cells 30 is available from a comparison with the time required to destroy the biopsy cells 32 when the means 12a is driven at the destructive frequency. If this is done, the means 12a should be driven at an intensity equal to that originally calculated for destroying the biopsy cells 32, and not at the higher intensity at which the means 12 is driven. Where the abnormal cells 30 define a growth of some thickness, the intensity of the ultrasonic transmission must be increased to insure destruction of the cells farthest from the means 12 in view of the attenuation losses resulting from transmission of the beam through the growth itself. Alternatively, the beam path through the patient may be altered as the destruction process proceeds.

If the target cells 30 occupy a volume in excess of the focal zone of the lens 20, the means 12 may be scanned over the target area to insure that all the cells 30 are destroyed. Such scanning can be effected by the stereotaxic device 28 once the location of the abnormal growth has been determined as described hereinabove. Preferably, such scanning is carried out automatically by the computer 27, in which data defining the locus of the cells 30 has been stored. Assuming the computer 27 is provided with a data base defining the anatomy of the patient 14, the computer may be programmed to continuously adjust the intensity of the ultrasonic transmission to compensate for the continuous changes in the transmission path during scanning. It will be apparent, however, that destruction of the cells 30 according to the present invention does not depend on precise focusing of the destructive beam. Thus, because the present invention relies upon the phenomenon of resonance, rather than heating, to destroy the abnormal cells 30, impacting of adjacent healthy cells by the beam will not destory those cells. Therefore, it is sufficient if the beam is scanned to impact the entire abnormal growth, without particular regard to whether or not the neighboring healthy cells are impacted in the process.

Where the number of target cells 30 is not excessive, it is contemplated that the dead cells will be carried out of the body by the body's normal waste system. However, where a large growth is involved, it may be necessary to surgically remove the dead cells. However, even where surgical removal is required, the technique described hereinabove is not redundant since it is well known that conventional surgical techniques often do not result in complete removal of the abnormal cells. In fact, to avoid this problem surgeons often remove healthy surrounding tissue.

Where surgery is used to remove cells destroyed by the method and apparatus of the present invention, healthy surrounding tissue may be left intact. Any dead abnormal cells left in the body as a result will be carried out by the body's waste system. In any event, inasmuch as they have already been destroyed, such cells will not cause any further damage to the body.

Thus far, the method and apparatus of the present invention have been described in connection with destruction of a localized abnormal cell growth. However, as will now be described, the technique is particularly suited for destroying non-localized and transient abnormal cells growths as well. For example, some cancers are characterized by excessive or abnormal cells in the blood. In the case of leukemia, there is an excess of leukocytes in the blood. Because these leukocytes are transient, conventional surgical techniques are useless.

To destroy the excess leukocytes utilizing the apparatus and method of the invention, it is necessary, as heretofore described, to first determine the resonant frequencies and corresponding damping coefficients of the leukocytes. An impact site for the ultrasonic radiation is then chosen and the losses resulting from transmission through the intervening body tissue are calculated. Using the techniques described hereinabove, the optimum resonant frequency for destroying the leukocytes is then selected taking into accourt the need to avoid damage to intervening body tissue. The required intensity for the destructive beam may then be determined.

Inasmuch as blood is continuously circulated throughout the body, it is not necessary to impact the entire body with ultrasonic radiation to effect destruction of the leukocytes. Rather, one or more sites may be selected and the ultrasonic bursts continued until sufficient leukocytes have been destroyed. The sites are preferably chosen to minimize the intervening body tissue. For example, the extremities may be selected. In such case, a plurality of transducer means 12 may be employed, each coupled to a stereotaxic device to accommodate scanning and focus. Alternatively, the blood may be circulated outside the body for impacting by the means 12, thereby avoiding the continuous impacting of intervening body tissue.

Skin cancer, often found over several areas of the body, may also be effectively treated by the method and apparatus of the invention. Following the teachings of the present invention, the optimum destructive beam is selected. Inasmuch as there is no intervening tissue between the skin cancer cells and the transducer means 12, and thus minimal transmission losses, a precisely focused beam of ultrasonic radiation is not required. Instead, and as shown in FIG. 3, the patient may be submerged in a tank 50 filled with a su ble liquid, such as water 52. As shown, a piezoelectric crystal 54 is secured against one sidewall of the tank 50 and is driven by the rf generator 56. The rf generator 56 is then adjusted to drive the crystal at the selected frequency with sufficient intensity to destroy the cancerous cells. In FIG. 3, the water medium 52 serves the same purpose as the water medium described above in connection with the system illustrated in FIG. 1, namely, to minimize transmission losses between the crystal 54 and the patient 58. To insure impacting of the entire body with radiation from crystal 54, it may be necessary to reposition the patient 58 from time to time.

Those skilled in the art will appreciate that the preferred method and apparatus of the present invention as described hereinabove may be modified once this description is known. For example, the ordering of the steps of the method of the invention may be varied. In one such variation, the step of selecting the preferred transmission path through the patient 14 to the cells 30 is carried out first. The resonant frequencies of the cells 32 are then determined, whereupon some of them may be immediately eliminated as a suitable destructive frequency because they impart too great a resonant effect to the intervening body tissue. The damping coefficients of the cells 32 at the remaining resonant frequencies are then calculated, and the resonant frequency at which the cells 32 exhibit the lowest damping coefficient selected as the optimum frequency for the destructive beam. Thereafter, it is only necessary to determine the intensity required to destroy the cells 30 at the selected frequency. It will also be apparent that although the method and apparatus of the invention have been particularly described in connection with the destruction of selected cells in human patient, use with all manner of living things, i.e. animals, plants, microorganisms, etc. is possible. Accordingly, in the claims, the term "host" should be understood to include all such living things.

Since these as well as other changes and modifications are intended to be within the scope of the present invention, the above description should be construed as illustrative and not in a limiting sense, the scope of the invention being defined by the following claims.

What is claimed is:

1. A method for destroying selected cells in a host without damage to non-selected cells, comprising:
    selecting a transmission path from an energy source to the selected cells;
    determining one or more of the resonant frequencies of the selected cells;

comparing the transmissibility of the selected cells at said one or more resonant frequencies with the transmissibility of the non-selected cells in the transmission path at said one or more resonant frequencies;

selecting, as a destructive frequency, one of said one or more resonant frequencies at which the transmissibility of said selected cells is higher than the transmissibility of said non-selected cells in the transmission path; and transmitting energy from said source at said destructive frequency along said transmission path with sufficient intensity to destroy said selected cells without destroying said non-selected cells in the transmission path.

2. The method according to claim 1, wherein said resonant frequency determining step comprises impacting a biopsy of said selected cells with energy over a predetermined frequency range corresponding to the expected range of said one or more resonant frequencies; and detecting the movement of said selected cells during said impacting.

3. The method according to claim 1, wherein said destructive frequency selecting step comprises:

determining the damping coefficients of said selected cells at said one or more resonant frequencies whereby the transmissibility of said selected cells at said one or more resonant frequencies may be determined; and determining the resonant frequencies and corresponding damping coefficients of said non-selected cells in said transmission path whereby the transmissibility of said non-selected cells at said one or more resonant frequencies may be determined.

4. The method according to claim 1, wherein said energy transmitting step further comprises disposing a coupling medium between said energy source and said host.

5. The method according to claim 1, wherein said energy transmitting step further comprises moving said energy source relative to said host for varying the impact site of said transmitted energy.

6. The method according to claim 1, wherein said energy transmitting step includes the step of determining the transmission losses resulting from transmission of said energy through said path.

* * * * *